United States Patent [19]

Tiitto

[11] Patent Number: 4,634,976
[45] Date of Patent: Jan. 6, 1987

[54] BARKHAUSEN NOISE METHOD FOR STRESS AND DEFECT DETECTING IN HARD STEEL

[75] Inventor: Seppo I. Tiitto, Pittsburgh, Pa.

[73] Assignee: American Stress Technologies, Inc., Pittsburgh, Pa.

[21] Appl. No.: 539,006

[22] Filed: Oct. 4, 1983

Related U.S. Application Data

[63] Continuation-in-part of Ser. No. 491,981, May 5, 1983, abandoned.

[51] Int. Cl.⁴ .................. G01N 27/82; G01R 33/12; G01L 1/12
[52] U.S. Cl. ........................ 324/240; 73/779; 324/209; 324/262
[58] Field of Search ........ 324/209, 228, 230, 239–243, 324/262; 73/587, 779, 801

[56] References Cited

U.S. PATENT DOCUMENTS

| | | | |
|---|---|---|---|
| 2,266,620 | 12/1941 | Coffman | 324/230 |
| 3,427,872 | 2/1969 | Leep et al. | 324/209 X |
| 3,449,664 | 6/1969 | Smith | 324/235 |
| 3,611,119 | 10/1971 | Madewell | 324/228 |
| 4,314,203 | 2/1982 | Haberlein | 324/262 |
| 4,409,549 | 10/1983 | Garner et al. | 324/262 |
| 4,445,089 | 4/1984 | Harrison | 324/262 X |
| 4,507,609 | 3/1985 | Madewell | 324/230 |

FOREIGN PATENT DOCUMENTS

| | | | |
|---|---|---|---|
| 171640 | 11/1965 | U.S.S.R. | 324/228 |
| 655956 | 4/1979 | U.S.S.R. | 324/228 |
| 667922 | 6/1979 | U.S.S.R. | 324/228 |

OTHER PUBLICATIONS

Karjalainen et al, "Detection of Plastic Deformation . . . by the Measurement of Barkhausen Noise", *NDT International*, Apr. 1979, pp. 51–55.

Primary Examiner—Gerard R. Strecker
Attorney, Agent, or Firm—Robert D. Yeager

[57] ABSTRACT

A sensor for a system that detects stresses and defects in a metal piece by employing the Barkhausen phenomenon enables static or dynamic testing of such metal pieces as hard steel in which only low levels of Barkhausen noise can be generated or which are configured in one of a large variety of shapes. The sensor includes apparatus that ensures that a uniform time-varying magnetic field can be produced in all the metal pieces of a variety of shapes. The sensor can include an energizing coil assembly which generates the magnetic field in the metal piece having a core constructed from such a material in which a low level of magnetic noise is generated as ferrite. The level of the magnetic noise generated in the ferrite core is so low that, even if the magnetic noise is sensed by the sensing coil assembly, which receives the Barkhausen noise gererated within the metal piece, that noise cannot interfere with the higher levels of Barkhausen noise generated in all ferromagnetic metals, including hard steel. The dynamic sensor has apparatus, such as wheel assemblies, for maintaining an air-gap of a substantially constant depth between the specimen and the energizing and sensing cores. The dynamic sensor can also include an energizing core which can be reoriented relative to the sensor to determine the directional characteristics of stress and defects in the specimen.

1 Claim, 23 Drawing Figures

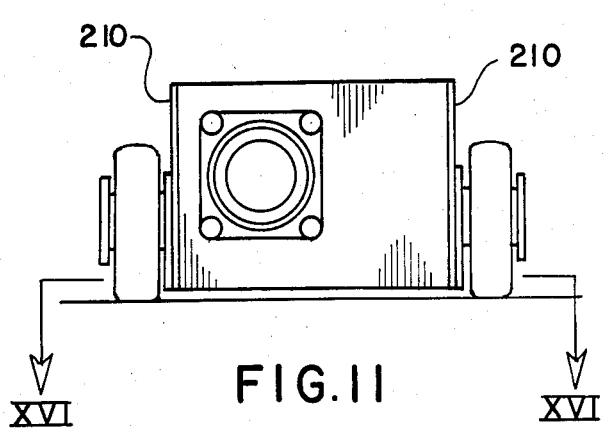
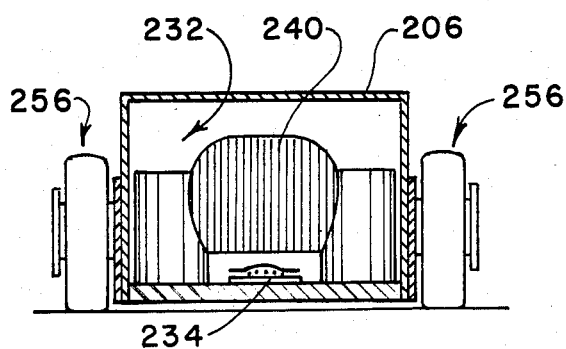
FIG.11  FIG.12
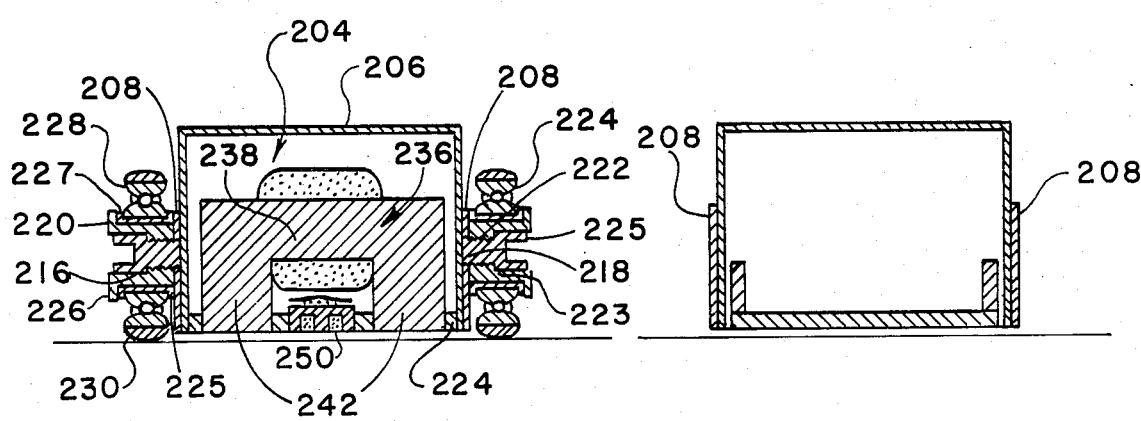
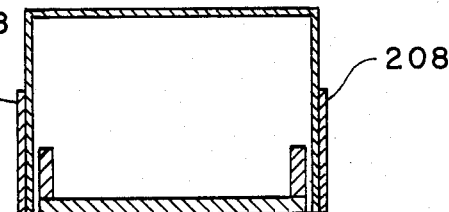
FIG.13  FIG.14
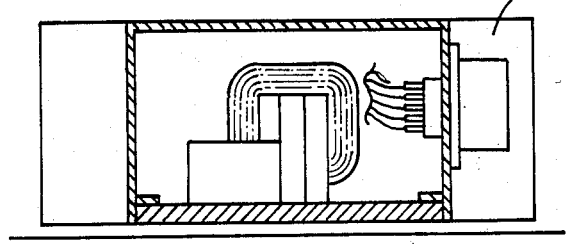
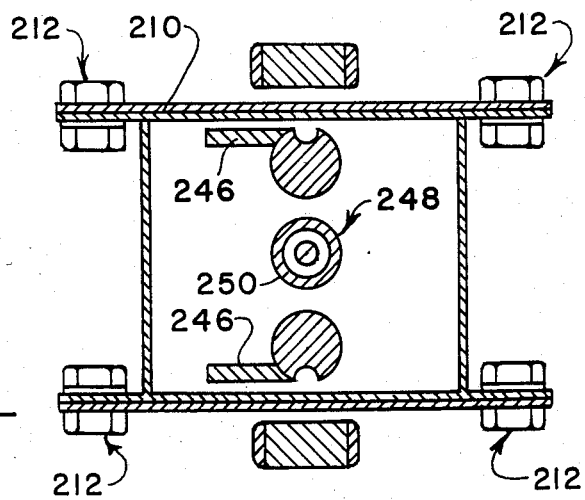
FIG.15  FIG.16

BARKHAUSEN NOISE METHOD FOR STRESS AND DEFECT DETECTING IN HARD STEEL

CROSS REFERENCE TO RELATED APPLICATION

This application is a continuation-in-part of applicant's prior copending application, Ser. No. 491,981, filed May 5, 1983, now abandoned.

BACKGROUND OF THE INVENTION

1. Field of the Invention

The present invention relates generally to stress and defect identification and, in particular, to a sensor for a system that employs magnetic fields to identify stress and defects in a metal piece.

2. Description of the Prior Art

Stress and structural defects in a metal piece and certain other properties of the metal piece can be identified by creating a time-varying magnetic field within the metal piece and analyzing the magnetic noise created in the metal piece by the magnetic field. In particular, one method employs a phenomenon known as the "Barkhausen effect" to identify stresses and defects in a metal piece. As is stated in column 2 of U.S. Pat. No. 3,427,872 ("the Leep et al. patent"), the Barkhausen effect is "defined in Webster's New International Dictionary (3rd Edition) as 'a series of abrupt changes or jumps in the magnetization of a substance when the magnetizing field is gradually altered'". The abrupt jumps that occur in the magnetization as the intensity of the field is changed can be detected as electrical noise by a sensing coil disposed proximate or in contact with the metal piece. The noise carried by the electrical leads from the coil—commonly referred to as "Barkhausen noise"—can be fed through a suitable processing network and, if desired, to a speaker. The level of the Barkhausen noise that is generated at a location within a metal piece depends in part on the sense, magnitude and direction of the stress at that location and the microstructure of the metal. Accordingly, workers in the art have attempted to employ the Barkhausen effect and Barkhausen noise to identify stresses and defects in and some microstructural characteristics of a metal piece. A discussion of the Barkhausen effect can be found in columns 1 and 2 of the Leep et al. patent.

Most systems which employ the Barkhausen effect to identify stresses and defects in a metal piece include an energizing coil assembly and a sensing coil assembly. The energizing coil is disposed proximate the location of the metal piece under examination and is energized with a periodically time-varying signal to induce in the metal piece a periodically time-varying magnetic field. The time-varying magnetic field in the metal piece causes abrupt jumps in the magnetization of the metal piece to occur. A sensing coil is disposed near or in contact with the metal piece near the same location and detects the abrupt jumps in the magnetization and converts those jumps to Barkhausen noise on the electrical conductor of the coil. The Barkhausen noise is then fed to circuitry, usually located externally of the sensor, which can process the noise in a variety of manners, depending upon the type of information to be obtained and displayed. Ultimately, the processed Barkhausen noise is fed to a device which displays it. A system for energizing the energizing coil assembly and processing the Barkhausen noise, and a description of displays of Barkhausen noise are described in the Leep et al. patent.

Known Barkhausen sensors are suggested for use in either static or dynamic applications. Static testing involves making a relatively small number of inspections of a single piece or of each of a relatively small number of pieces. That limitation is imposed by the fact that most sensors used in static testing require physical contact between the energizing core of the energizing coil assembly and the test piece. Therefore, changing the location of inspection requires removing the sensor from the test piece and moving it into contact with the next inspection site to prevent rapid and undesirable wear of the energizing core that would result from moving the sensor from test site to test site while the core is in contact with the piece. Dynamic testing is employed in situations where the entire surface of a single metal piece must be tested or where more than one location of each of a number of test pieces must be inspected. The sensor used in dynamic testing does not require physical contact between the energizing and sensing coil assemblies and the metal piece. Therefore, there can be constant relative movement between the metal pieces under examination and the sensor.

Any system employing Barkhausen noise to locate stress and defects within a specimen depends, for proper functioning, upon the phenomenon that the level of Barkhausen noise generated in a specimen changes significantly when the sensor is moved between a location where no stress or defects exist and a location where stress or a defect is located. Therefore, variations in the level of Barkhausen noise generated in the metal piece caused by the examining process itself must be minimized to the point where proper analysis of the Barkhausen noise is not prevented. Accordingly, the effects on the generated Barkhausen noise due to magnetic self-coupling within the Barkhausen sensor, inconsistent magnetic coupling between the sensor and the metal piece and variations in the shapes of metal pieces must be minimized.

Magnetic self-coupling can occur between the energizing and sensing coils of the sensor. Often, it is necessary to examine a metal piece constructed of hard steel, in which only low levels of Barkhausen noise can be generated. The term "hard steel", as used herein, means steel having a Rockwell C hardness greater than about 50. Exemplary of such steels are (i) martensitic steels that have been either quenched or quenched and tempered; (ii) fine grained, high strength alloy steels; and (iii) carburized steels. Generally, the cores of the energizing coil assemblies of conventional Barkhausen sensors are fabricated from iron or steel. A relatively high level of magnetic noise is generated within iron and steel as the magnetic field induced in the iron or steel is varied. Accordingly, a high level of magnetic noise is generated within an iron or steel energizing core, which can be sensed by the sensing coil assembly and interferes with the low level Barkhausen noise generated in a hard steel piece.

Nonetheless, steel or iron has been used consistently as the material for energizing coil assembly cores—even for examining hard steel—for, generally, two reasons. First, the periodic signal used to energize the energizing coil assembly is of a rather low frequency. Electromagnetic devices which operate under low frequency commonly have cores constructed of iron or steel. Second, the relatively high noise generated in an iron or steel energizing core can interfere with Barkhausen noise generated in a test piece only if the energizing core and sensing coil assembly are located sufficiently proximate each other to permit electromagnetic coupling of the noise between the energizing core and sensing coil assembly. When conventional Barkhausen systems have been used to test hard steel for stress or defects, they have been used only in experimental settings and only on large pieces. Accordingly, the energizing core of the sensor has been large and, therefore, spaced a sufficient distance from the sensing coil assembly to prevent electromagnetic coupling from occurring.

However, in commercial applications, metal pieces with small cross-sectional areas must be examined. Therefore, the sensor used to examine those metal pieces must be small and the distance between the energizing core and sensing coil assembly must be reduced from that of experimental sensors. Destructive electromagnetic coupling occurs between the energizing core and sensing coil assembly, which makes it impossible to distinguish the low level Barkhausen noise generated in a hard steel piece from the high noise generated in the iron or steel energizing core. Therefore, there exists a need for a Barkhausen sensor which generates lower intrinsic noise than conventional Barkhausen sensors, and that permits distinguishing the intrinsic sensor noise from the Barkhausen signal obtained from the metal piece.

Proper magnetic coupling between the sensor and the metal piece can be achieved in several ways. A Barkhausen sensor having an energizing core that is adapted to contact the metal piece shall be referred to hereinafter as a "contact sensor". Since the magnitude of the magnetic field induced in a metal piece, and, accordingly, the level of the Barkhausen noise generated within the piece, by a contact sensor depends on the magnitude of the area of the core of the energizing coil assembly that is in contact with the metal piece, the same sensor will provide different readings for different magnitudes of contact area, making interpretation of the results difficult. Since conventional contact sensors have been employed only under experimental conditions, each sensor has been adapted for use with metal pieces of only one general shape. When used with that shape, a given constant magnitude of contact area is achieved. If the sensor were to be used in a commercial setting, the magnitude of the areas of the sensor and the metal pieces which are in contact with each other would vary with the shape of the metal piece. Thus, the magnitude of the Barkhausen noise that indicates existence of a defect would vary with the shape of the metal piece and, accordingly, analysis of the signals received from the sensor would be unduly difficult. Therefore, there exists a need for a Barkhausen contact sensor which either provides constant contact area between the metal piece and the sensor, regardless of the shape of the metal piece, or electrically maintains a uniformly varying magnetic field among metal pieces of various shapes.

A Barkhausen sensor having an energizing core that is not adapted to contact the metal piece under examination shall be referred to hereinafter as "air gap sensor". Use of an air gap sensor requires the existence of an air gap between the energizing and sensing coil assemblies and the metal piece. Generation by the sensor of intelligible information, in the form of Barkhausen noise, depends on the maintenance of an air gap of uniform depth throughout the examination area defined by the sensor and upon maintenance of an air gap of a constant depth from inspection point to inspection point either within the same metal piece or among metal pieces. If dynamic or continuous examination of a metal piece or pieces is desired, an air gap of a constant depth must be maintained during the period of relative movement between the metal pieces under examination and the sensor. Accordingly, there is a need for a Barkhausen sensor that provides an air gap of a consistent configuration during performance of static or dynamic examination.

Finally, the thickness of the metal piece itself can change the level of Barkhausen noise generated within the metal piece. Accordingly, examination of metal pieces of different thicknesses can require constant calibration of the system that analyzes the Barkhausen noise and makes it available for inspection. Because interpreting Barkhausen noise differently for different thicknesses of metal pieces is unduly inconvenient, it is common to normalize the system each time the thickness of the test piece changes by altering the magnitude of the current supplied to the energizing coil assembly. The proper current level can be determined in advance experimentally for different thicknesses of metal pieces.

Known Barkhausen sensors have not successfully addressed the concerns described above. Because of its low intrinsic Barkhausen noise level, it has been proposed in Finland Patent No. 51873 to use ferrite as the core material for a Barkhausen noise sensor adapted to investigate flat metal pieces; however, in that proposal, a single coil serves as both the energizing coil and the sensing coil. The result of that arrangement is that the sensing coil tends to detect the intrinsic noise of the core material rather than the noise induced in the specimen. This is especially the case when measuring hard steels in which only low levels of Barkhausen noise can be generated. Accordingly, that arrangement cannot be successfully used to detect Barkhausen noise in hard steels due to magnetic self-coupling occurring within the sensor.

An article entitled "Measurement of Barkhausen Noise On Moving Steel Sheet with Non-Contact Sensor", published in Finland by Markku Pesonen, discloses a concept for dynamically measuring Barkhausen noise generated in a steel sheet. FIGS. 5.3(a) and (b) of the publication illustrate the sensors in diagrammatic form. FIG. 5.3(a) shows a DC sensor having energizing coils energized by a DC source and FIG. 5.3(b) shows an AC sensor having energizing coils energized from an AC source. Both sensors employ identical sets of energizing and sensing coils on both sides of a steel sheet to reduce the effect of vibration of the sheet. The DC sensor employs two sets of energizing coils, each set of which is energized by a DC source of a polarity opposite to that which energizes the remaining set. The DC sensor relies on movement of the sheet relative to the coils to generate a time varying magnetic field, which causes Barkhausen noise to be generated, in the sheet.

Several problems are experienced through use of the DC sensor shown in FIG. 5.3(a). First, the DC sensor can be used to test only relatively soft metal pieces if the piece must be moved at a slow speed. At slow speeds, insufficient Barkhausen noise is generated within hard metal pieces. Examples of metal pieces which must be moved at a low rate of speed include odd shaped pieces which simply cannot be moved rapidly. Further, variations in the speed of movement of the metal sheet under observation change the "frequency" of the apparent time-varying field and introduces substantial variation in the generated Barkhausen noise that is not due to the presence or absence of stress or defects. Finally, the AC and DC sensors shown in FIGS. 5.3(a) and (b) are suitable only for inspection of flat, relatively thin metal sheets, which is a serious limitation on their use. Accordingly, the DC and AC sensors do not provide Barkhausen sensors that are practical for use during dynamic testing.

Accordingly, there exists a need for a sensor that minimizes magnetic coupling within the sensor. Further, there is a need for a sensor that provides proper coupling between the sensor and metal pieces of differing shapes and thicknesses.

SUMMARY OF THE INVENTION

The present invention provides contact and air gap sensors that can be used to statically or dynamically detect stress and defects in metal pieces of a large variety of microstructures, compositions, sizes and shapes.

The sensors are particularly useful in nondestructively inspecting relatively small pieces of hard steel, which represent a large proportion of metal pieces that must be tested in a commercial setting. Further, the prolems of magnetic self-coupling and maintenance of proper magnetic coupling between the sensor and the test piece have been so minimized that only one set of criteria for determining defects from measured Barkhausen noise levels need be established and used for all shapes and sizes of metal pieces of the same composition and microstructure.

The present invention provides sensors for use with a system that provides information related to the stress and defects in a metal piece by generating a magnetic field in the metal piece. The sensor includes an energizing coil assembly including an electrical conductor wound around a ferrite core. The energizing coil assembly is adapted to receive a periodic time-varying electrical signal which will induce in the metal piece, when the ferrite core is located proximate the metal piece, a time-varying magnetic field. The sensor also includes a sensing coil assembly including a second electrical coil which is so disposed relative to the energizing coil assembly and, when the ferrite core is located proximate the metal piece, to the metal piece as to permit the sensing coil assembly to detect noise generated within the metal piece by the induced magnetic field. The sensing coil of the present invention is physically and electrically independent of the energizing coil assembly.

Preferably, for static testing, the ferrite core and the sensing coil assembly are adapted to make contact with the metal piece. Preferably, the magnetic field inducing apparatus includes a pair of contacts defined by the ferrite core. The contacts are so oriented in shape that uniform contact can be maintained between the ferrite core and the metal piece. The contacts can be rounded to permit a constant magnitude of contact area between the energizing coil assembly and metal pieces of a variety of shapes.

Preferably, the static sensor also includes apparatus associated with at least one of the energizing coil assemblies and the sensing coil assembly for ensuring that uniform contact is maintained between the metal piece and the sensing coil assemblies. Preferably, the ensuring apparatus includes a device for urging the sensing coil assembly into contact with the metal piece when the energizing coil assembly is in contact with the metal piece and is an elastic, nonmagnetic member.

Preferably, the air gap sensor of the present invention that is adapted for use as a dynamic test instrument includes apparatus for maintaining an air gap of substantially constant depth between the ferrite core and the metal piece when there exists movement of the ferrite core relative to the metal piece. The air gap sensor can include apparatus for reorienting the ferrite core relative to the metal piece to reorient the induced magnetic field within the metal piece. The dynamic sensor can include a housing for containing the ferrite core and a table mounted for rotation with respect to the housing to which the ferrite core is mounted. The maintaining apparatus can be a pair of wheels that so cooperate with the ferrite core that the sensor can be rolled along the metal piece to dynamically test it for stress and defects. Further, the maintaining apparatus can be a spacing member constructed of a suitable nonmagnetic, wear-resistant material —such as Teflon ®, nylon or austenitic stainless steel—that is disposed between the energizing and sensing coil assemblies and is in contact with the metal piece during normal use of the sensor. Also, the maintaining apparatus can establish an air cushion between the metal piece and the sensor, which is mounted to a stationary object.

The present invention also provides a sensor capable of inducing in the test piece at least two magnetic fields, each oriented in a different direction from that of the other.

BRIEF DESCRIPTION OF THE DRAWINGS

The following detailed description of the preferred embodiments can be understood better if reference is made to the accompanying drawings in which:

FIG. 11 is a rear view of the sensor shown in FIG. 9;

FIG. 12 is a sectional view of the sensor shown in FIG. 10 taken along the line XII—XII;

FIG. 13 is a sectional view of the sensor shown in FIG. 10 taken along the line XIII—XIII;

FIG. 14 is a sectional view of the sensor shown in FIG. 10 taken along the line XIV—XIV;

FIG. 15 is a sectional view of the sensor shown in FIG. 10 taken along the line XV—XV;

FIG. 16 is a sectional view of the sensor shown in FIG. 11 taken along the line XVI—XVI;

DETAILED DESCRIPTION OF THE PREFERRED EMBODIMENTS

Figure 1:
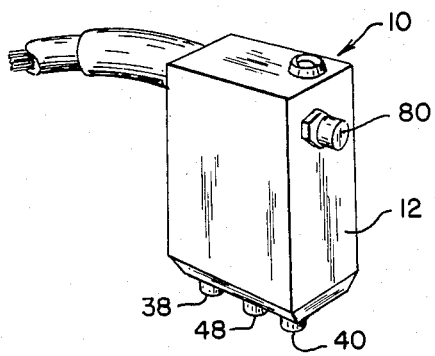
FIGS. 1 and 2 are isometric views of a sensor constructed according to the provisions of the present invention.
Figure 2:
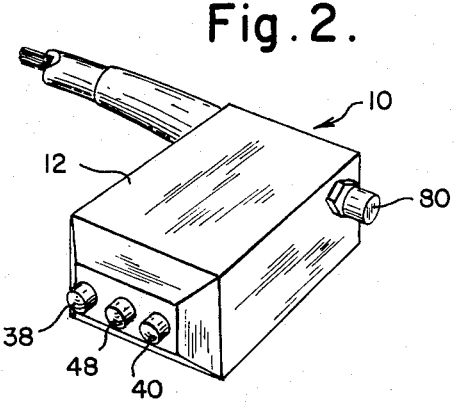
Figure 3:
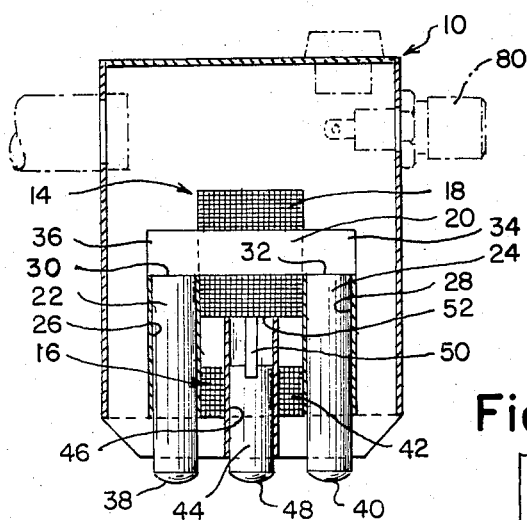
FIG. 3 is a front, sectional view of the sensor shown in FIGS. 1 and 2.
Figure 4:
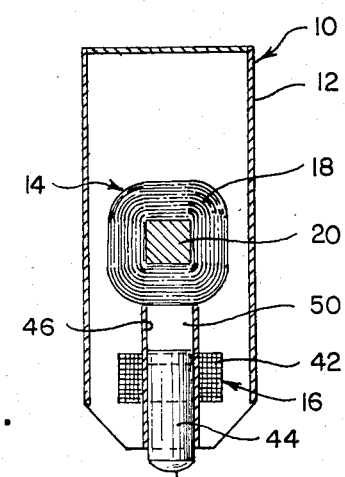
FIG. 4 is a side, sectional view of the sensor shown in FIGS. 1 and 2.

FIGS. 1-5 show a static sensor 10, a preferred embodiment of the present invention. Static sensor 10 is particularly adapted for testing where only a relatively small number of readings need to be taken since sensor 10 should be disengaged from one test site before it is moved to a different test site. Sensor 10 includes a housing 12 which contains an energizing coil assembly 14 and a sensing coil assembly 16 suitably mounted therein by conventional means (not shown).

Energizing coil assembly 14 includes an electrical conductor 18 which is wound around ferrite base 20. A pair of ferrite legs 22 and 24 are disposed within fittings 26 and 28, respectively, of housing 12. Preferably, base 20 and legs 22 and 24 are constructed, for instance, from such a manganese oxide based ferrite material as that sold under the trademarks PHILIPS 3C6 or 3C8 by Philips A. G. Seats 30 and 32 are adapted to be in contact with ends 34 and 36, respectively, of ferrite base 20. Legs 22 and 24 define rounded contacts 38 and 40, respectively, which are adapted to contact the metal piece under examination. Legs 22 and 24 are held by friction within fittings 26 and 28 and can be removed to reshape contacts 38 and 40 and then replaced within fittings 26 and 28. Conductor 18 receives a periodically time-varying signal from any suitable conventional source. When contacts 38 and 40 are in contact with a metal piece, the periodic electrical signal induces a magnetic field in ferrite base 20 and ferrite legs 22 and 24, which causes the metal piece to become magnetized between contacts 38 and 40 of legs 22 and 24. The varying magnetic field generated by energizing coil assembly 14 causes abrupt jumps in the magnetization of the metal piece, known as the Barkhausen effect, to occur. The rounded contacts 38 and 40 of legs 22 and 24 permit point contact to be established between legs 22 and 24 and metal pieces of a variety of shapes.

Sensing coil assembly 16 includes an electrical coil 42 disposed within container 12 and wound around a ferrite sensing core 44. Sensing core 44 is secured to an elastic silicone member 50, which is held by friction within fitting 46 of case 12. Contact 48 of core 44 is rounded to permit point contact between sensor 10 and metal pieces of a variety of shapes. Core 44 can be removed from fitting 46, to reshape contact 48 of core 44, and subsequently replaced. Member 50 urges core 44 away from passage base 52 and into contact with the metal piece under examination, but cannot expel core 44 completely from within fitting 46. The abrupt magnetic jumps occurring in the metal piece due to the magnetic field established by energizing coil assembly 14 induce electrical Barkhausen noise in coil 42 of sensing coil assembly 16 when contact 48 is in contact with the metal piece. The Barkhausen noise induced in coil 42 can be processed and displayed in any known desired fashion.

Figure 8:
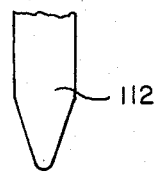
FIG. 8 is a side view of one of the converging-type contacts terminating in rounded edges in FIGS. 6 and 7.
Figure 5:
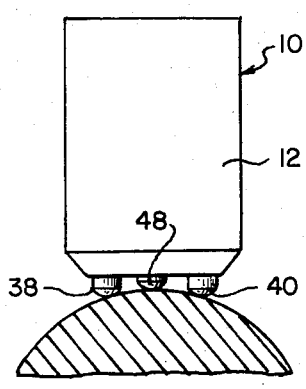
FIG. 5 is a front view of the sensor shown in FIGS. 1 and 2 being used to test the convex surface of a metal piece.
Figure 6:
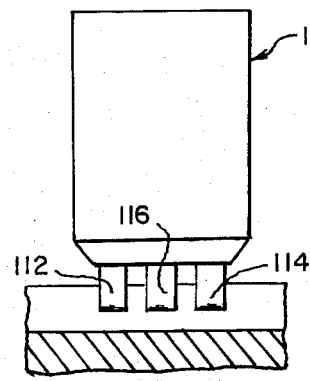
FIG. 6 is a front view of the sensor shown in FIGS. 1 and 2 being used to test a tooth of a metal gear.
Figure 7:
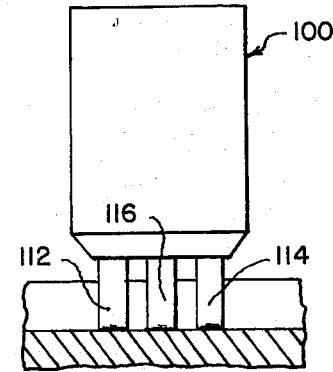
FIG. 7 is a front view of the sensor shown in FIGS. 1 and 2 being used to test the root of a metal gear.
Figure 9:
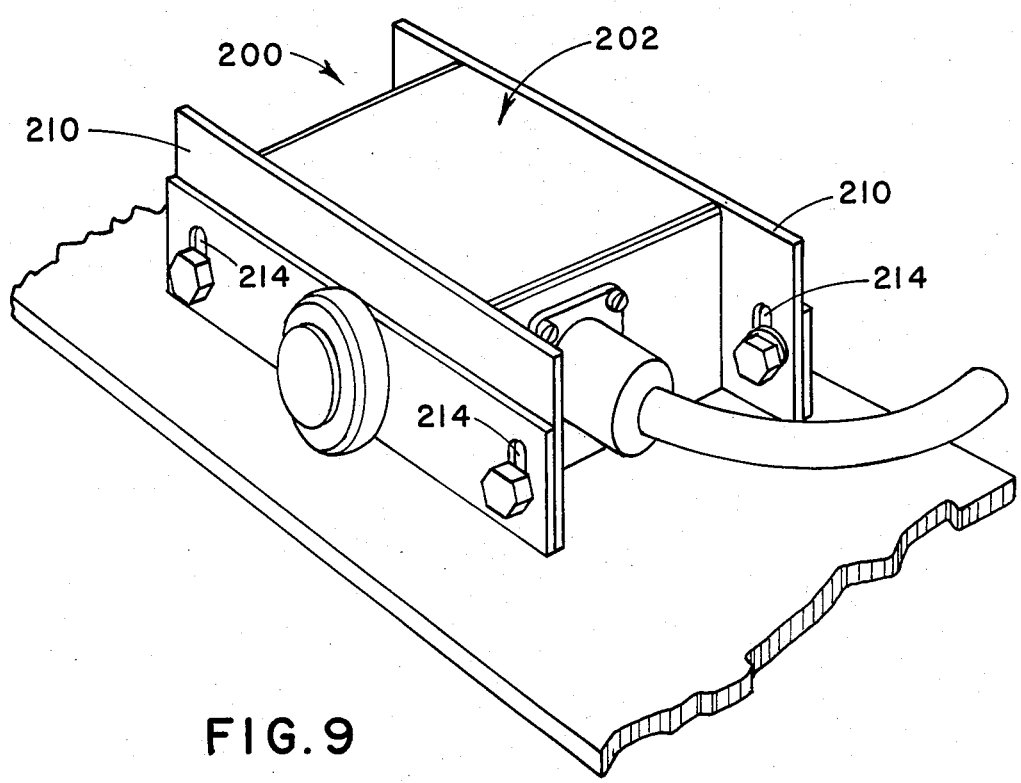
FIG. 9 is an isometric view of a dynamic sensor constructed according to the provisions of the present invention.
Figure 10:
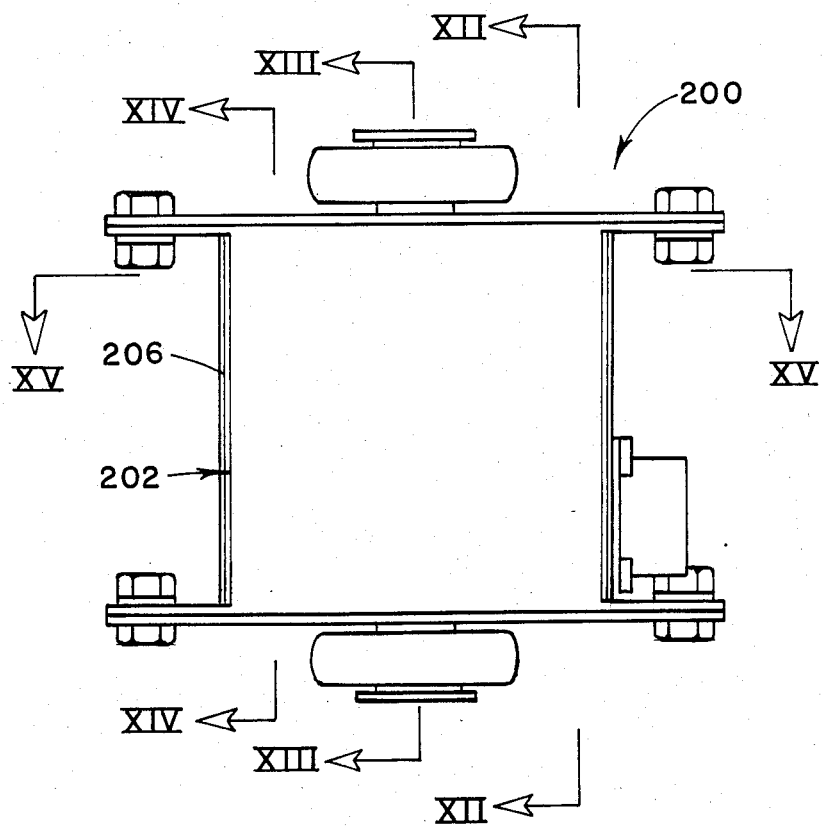
FIG. 10 is a top view of the sensor shown in FIG. 9.
Figure 17:
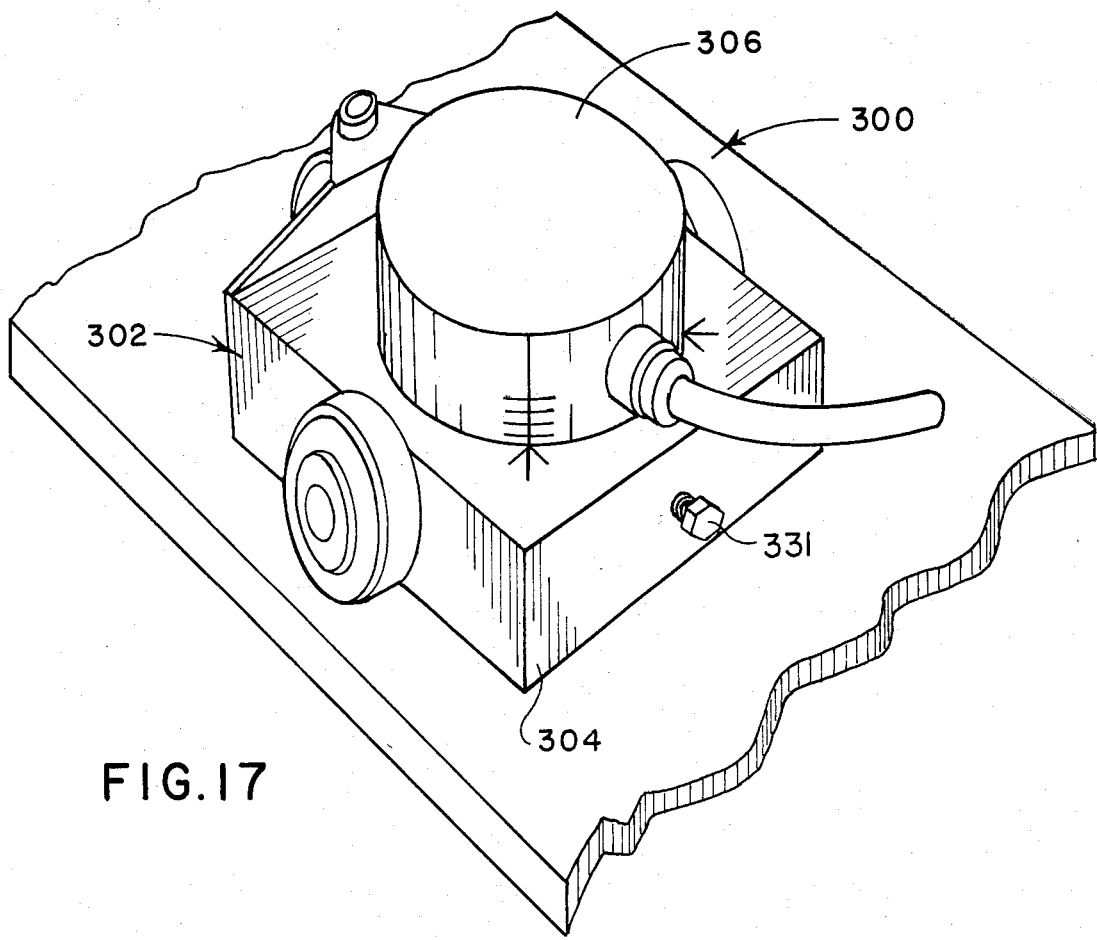
FIG. 17 is an isometric view of an alternate embodiment of the present invention.
Figure 18:
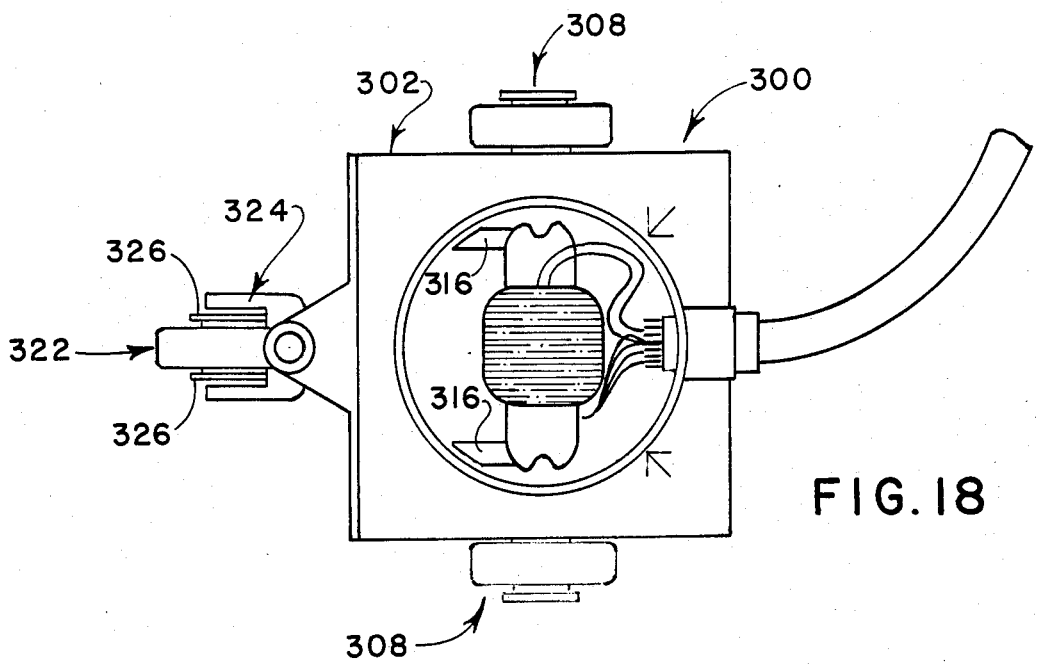
FIG. 18 is a section view of the dynamic sensor shown in FIG. 20 taken along the line XVIII—XVIII.
Figures 19, 20:
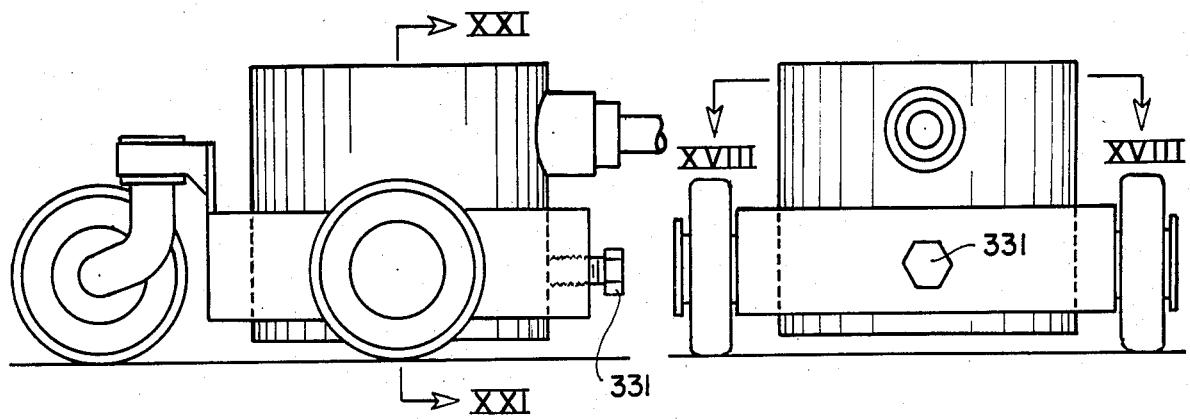
FIG. 19 is a side view of the sensor shown in FIG. 17.
FIG. 20 is a rear view of the sensor shown in FIG. 17.
Figure 21:
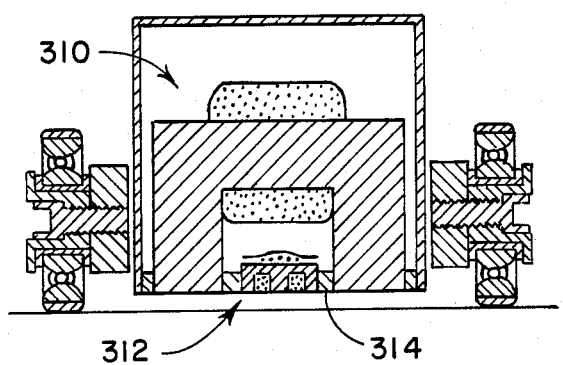
FIG. 21 is a sectional view of the sensor shown in FIG. 19 taken along the line XXI—XXI.
Figure 22:
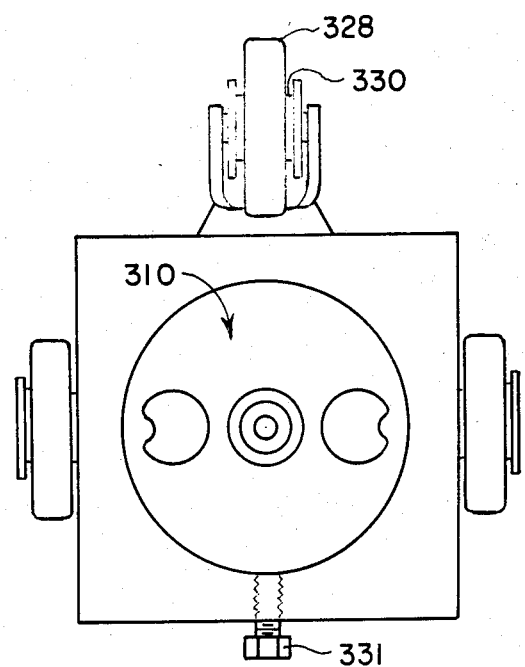
FIG. 22 is a top view of the sensor shown in FIG. 17.

FIGS. 6, 7 and 8 show sensor 100, an alternate embodiment of the present invention. Sensor 100 is identical to sensor 10, with the exception that core legs 22 and 24 and core 44 of sensor 100 define sections each of which includes two opposed converging sides defining rounded contact surfaces 112, 114 and 116, respectively. Contacts 112, 114 and 116, facilitate testing the teeth and roots of metal gears, as is shown in FIGS. 6 and 7.

To use sensor 10, contacts 38, 40 and 48 are brought into contact with the metal piece. A button 80, located on the exterior of case 12, is depressed to begin a test cycle. Depression of button 80 causes a predetermined number of cycles of the energizing electrical signal to be imposed across energizing coil assembly 14. Energizing coil assembly 14 causes a periodically time-varying magnetic field to be established in the metal piece. Sensing coil assembly 16 detects the magnetization jumps generated within the metal piece and converts them to an electrical signal. A conven-tional averaging circuit averages the level of the Barkhausen noise generated during the test cycle and provides the averaged signal to circuitry which processes and displays the noise in any desired known fashion.

Generally, sensor 100 is used in the same manner as that employed with sensor 10. The length of the test cycle should be chosen to ensure that a statistically sound value of Barkhausen noise is obtained.

An indicator light can be provided to indicate that a test cycle is in progress.

FIGS. 9 through 16 show sensor 200—another preferred embodiment of the present invention. Sensor 200 is particularly useful for dynamic testing, which is desirable where a very large number of locations is tested. Sensor 200 includes a housing assembly 202 which houses a magnetic assembly 204.

Housing assembly 202 includes a housing frame 206. A wheel plate 208 is mounted to the outside surface of each housing frame side panel 210 by four nut and bolt assemblies 212 which are assembled through openings formed in wheel plates 208 and side panels 210. Openings 214 formed in wheel plates 208 are elongated and permit vertical repositioning of each wheel plate 208 with respect to side panels 210.

A wheel assembly 256 is mounted to each wheel plate 208. Accordingly, vertical adjustment of wheel plate 208 with respect to housing frame 206 achieves adjustment of the distance between base plate 244 and the metal piece in contact with wheel assembly 256. Each wheel assembly 256 includes a wheel mount 220 which is secured to wheel plate 208 by a threaded wheel shaft 216. Shaft 216 is threaded into a threaded opening 222 formed in wheel mount 220 and opening 218 of wheel plate 208. Wheel mount 220 defines a recess 223 which receives head 221 of shaft 216. A rubber ring 225 is disposed around the outer surface of wheel mount 220 between flange 226 defined by wheel mount 220 and wheel plate 208. Rubber ring 225 dampens a substantial portion of the mechanical vibrations created when wheel assemblies 256 are rolling on a metal piece as it is being examined. Rubber ring 225 defines annual flanges 227 between which a ball bearing 224 is disposed on rubber ring 225. A wheel can be mounted on ball bearing 224. However, in sensor 200 a rubber tire 230 is disposed around the outer ring 228 of bearing 224 to eliminate the need for a wheel. Tire 230 aids in dampening mechanical vibrations created by wheel assemblies 256 as sensor 200 is used.

Magnet assembly 204 includes energizing coil assembly 232 and sensing coil assembly 234. Energizing coil assembly 232 includes energizing core 236 constructed of ferrite. An electrical conductor is wound around leg 238 of energizing core 236 to form an energizing coil 240. Legs 242 of energizing core 236 are secured within base 244 of housing frame 206. Legs 246 are secured to legs 242 of energizing core 236. Legs 246 provide structural support for energizing core 236.

Sensing coil assembly 234 includes a cylindrical sensing potcore 248 constructed of ferrite material within which an electrical conductor is wrapped to form sensing coil 250. Sensing coil assembly 234 is secured within an opening formed in base plate 244.

Sensor 200 operates in the same manner as sensor 10 except that a uniform magnetic field is maintained in the metal piece by wheel assemblies 256. Wheel assemblies 256 maintain an air gap of a substantially constant depth between the metal piece and sensing and energizing cores 248 and 236, respectively. Sensor 200 is adapted to roll along a metal piece on wheel assemblies 256 to continuously create Barkhausen noise along the surface of the metal piece. Sensing coil assembly 234 converts the Barkhausen noise to electrical noise which is provided along cable 258, which also provides magnetizing current for energizing coil assembly 232 and noise communication to the Barkhausen system. Sensor 200 can be used to investigate any metal piece which spans the distance between wheel assemblies 256. Continuous scanning can be achieved by either moving sensor 200 along the metal piece, by moving the metal piece with respect to sensor 200, or a combination of both. The dimensions of sensor 200 depend in part on the size of the metal pieces to be tested. If the dimensions of sensor 200 must be made very small, the two wheel assemblies 256 can be replaced by one wheel assembly or by a sheet of nonmagnetic, wear-resistant material secured to the bottom surface of base plate 244 and adapted to contact the metal piece. Alternately, sensor 10 could be converted to a dynamic sensor by encasing in epoxy the exposed ends of members 22, 24 and 44, shown best in FIG. 3, to provide a spacing member adapted to contact the metal piece. In such a case, the encased ends of member 22, 24 and 44 would define a shape similar to that shown in FIG. 8.

FIGS. 17 through 22 show a dynamic sensor 300, a further preferred embodiment of the present invention. Sensor 300 is particularly useful in applications where it is inconvenient or impossible to reorient the Barkhausen sensor with respect to the metal piece under observation to reorient the magnetic field induced in the metal piece by the energizing coil of the sensor. The energizing coil assembly of sensor 300 is mounted for rotation with respect to the housing sensor 300.

Sensor 300 includes a housing assembly 302, which includes a stationary portion 304 and a rotatable portion 306. Portion 306 may be manually rotated within stationary housing 304 to a new position and is there held in place by set screw 331. Wheel assemblies 308 are identical to wheel assemblies 256 of sensor 200 and are secured to sensor 300 in the same manner as wheel assemblies 256 are secured to sensor 200.

Rotatable housing 306 contains an energizing coil assembly 310 and a sensing coil assembly 312, both of which can be identical to sensing coil assembly 234 and energizing coil assembly 236, respectively, of sensor 200. Coil assemblies 310 and 312 are mounted to base plate 314 of rotatable housing 306 in the same manner as coil assemblies 232 and 234 are mounted to base 244 of sensor 200. Legs 316 are secured to legs 320 of energizing coil assembly 310.

A guide wheel assembly 322 is mounted to the front of sensor 300 to facilitate rotation of sensor 300 with respect to the metal piece under investigation, if desired. Fork 324 of assembly 322 is mounted for rotation about a vertical axis to a wheel mounting 326 which is secured to stationary housing 304. Wheel 328 is mounted for rotation on a shaft 330 between the legs of fork 324. Vibrations of the wheel assembly 322 have been damped in the same way as in the wheel assembly 256. Wheel assembly 322 is identical to wheel assembly 308 with the exception that it includes a second wheel mount.

Sensor 300 can be used in a fashion that is identical to use of sensor 200. However, if the directional characteristics of stress in a metal piece are desired to be determined or if the orientation of the energizing magnetic field within the metal piece is desired to be reoriented for some other reason, sensor 300 facilitates such reorientation. Guide wheel assembly 322 can be used to change the direction of travel of sensor 300 over the metal piece as the metal piece and sensor 300 move with respect to each other to reorient the energizing magnetic field with respect to the metal piece or to measure a full circle by rotating sensor 300 over one spot. Further, rotatable housing 306 can be rotated with respect to the stationary housing 304 to reorient the energizing core of energizing coil assembly 310 with respect to the motion of the metal piece relative to sensor 300, and therefore reorient the energizing magnetic field. Further, the position of rotatable housing 306 can be adjusted relative to stationary housing 304 to adjust the depth of the air gap between the metal piece and sensor 300.

Generally, as is known in the art, the resolution of the Barkhausen system depends on the frequency of the magnetic field induced in the metal piece and the relative speed between the sensor and the piece. Generally, at least one cycle of the magnetic field must be able to occur over the area of a defect in a metal piece before the system can detect the defect. The following table is offered as a general guideline for selecting the system magnetizing frequency:

| HIGHEST RELATIVE SPEED-(meters/second) | MAGNETIZING FREQUENCY (HZ.) | |
|---|---|---|
| | 2 cm. resolution | 4 cm. resolution |
| 1 | 50 | 25 |
| 5 | 250 | 125 |
| 10 | 500 | 250 |

The electrical noise caused by the mechanical vibration of the rolling wheels of sensors 200 and 300 also depends on the relative speed between the metal piece and the sensor. The Barkhausen system must filter this low frequency noise caused by the mechanical vibration. As a general guide, the system must eliminate all frequencies below 4 kHz for a sensor rolling at 1 m/sec., 10 kHz for a sensor rolling at 5 m/sec., and 20 kHz for a sensor rolling at 10 m/sec.

Figure 23:
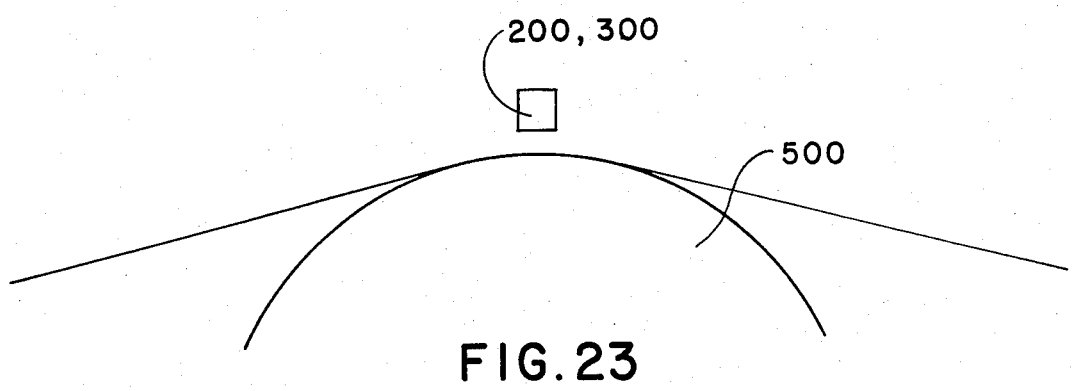
FIG. 23 is a diagrammatic view of an arrangement for dynamically examining a metal sheet.

As is shown in FIG. 23, sensors 200 and 300 can be adapted to the inspection of moving steel sheets, if the vibrations of the wheel are eliminated by a deflection drum 500 made of nonmagnetic material. In such an application, if the sheet is moving at a high speed, it is convenient to maintain the air gap with means other than wheels. In any application where relative movement of the sensor and the test piece occurs at high speed, proper spacing between the energizing and sensing coil assemblies and the test piece can be accomplished by suitably creating an air cushion between the sensor and the test piece. In such an application, the sensor would be rigidly mounted to a stationary object.

What is claimed is:

1. A method for generating information relative to the presence or absence of stress and defects in a piece of hard steel having at least one nonplanar surface comprising the steps of:

(a) providing a Barkhausen noise sensor having a magnetizing core composed of ferrite and a sensing coil assembly having a ferrite core;

(b) positioning the sensing coil assembly of said sensor relative to said magnetizing core thereof to cause, when said sensor is energized, Barkhausen noise generated by electromagnetic coupling between said magnetizing core and said sensing coil assembly to be less intense than Barkhausen noise generated within said piece of steel;

(c) effecting simultaneous contact by said magnetizing core and said core of said sensing coil assembly with said nonplanar surface of said piece of steel;

(d) generating Barkhausen noise within said piece of steel; and (e) sensing the Barkhausen noise so generated to develop said information.

* * * * *